United States Patent [19]
Bolt et al.

[11] Patent Number: 5,962,022
[45] Date of Patent: Oct. 5, 1999

[54] PHARMACEUTICAL FORMULATION WITH EFFERVESCENT COUPLE

[75] Inventors: Ian James Bolt; David Roy Merrifield; Paul Laurence Carter, all of Worthing, United Kingdom

[73] Assignee: SmithKline Beecham plc, Brentford, United Kingdom

[21] Appl. No.: 08/346,846

[22] Filed: Nov. 30, 1994

Related U.S. Application Data

[63] Continuation of application No. 08/081,964, Jun. 24, 1993, which is a continuation of application No. 07/515,200, Apr. 27, 1990, Pat. No. 5,225,197.

[30] Foreign Application Priority Data

Apr. 28, 1989 [GB] United Kingdom .................. 8909793

[51] Int. Cl.$^6$ ....................................................... A61K 9/46
[52] U.S. Cl. ............................................ 424/466; 424/441
[58] Field of Search .................................. 424/440, 466, 424/441

[56] References Cited

U.S. PATENT DOCUMENTS

| 4,639,368 | 1/1987 | Niazi et al. | 424/48 |
| 4,952,402 | 8/1990 | Sparks et al. | 424/440 |
| 5,178,878 | 1/1993 | Wehling et al. | 424/466 |

*Primary Examiner*—Thurman K. Page
*Assistant Examiner*—William E. Benston, Jr.
*Attorney, Agent, or Firm*—Dara L Dinner; Stephen Venetianer; Charles M Kinzig

[57] ABSTRACT

A chewable tablet comprises a medicament dispersed in a chewable base, such as mannitol, together with an effervescent couple, such as citric acid-sodium bicarbonate. The combination of effervescence and chewability with optional flavorings improves the taste characteristics of the medicament in oral administration. A disintegrant such as microcrystalline cellulose may be added to give the patient the option of dispersing the tablet in water.

12 Claims, No Drawings

PHARMACEUTICAL FORMULATION WITH EFFERVESCENT COUPLE

CROSS-REFERENCE

This is a continuation of Ser. No. 08/081,964 filed Jun. 24, 1993 which is a continuation of Ser. No. 515,200 filed Apr. 27, 1990, now U.S. Pat. No. 5,225,197.

This invention relates to pharmaceutical compositions for oral administration of antibiotics and other medicaments with unpleasant taste characteristics, and particularly to compositions formulated as chewable tablets.

From the point of view of bioavailability, the preferred form of administration of sparingly soluble medicaments such as a β-lactam antibiotics is often an aqueous suspension. However, there are problems associated with this form of administration. For example, such preparations in multi-dose form may have a limited shelf life; and usual methods of dose measurement lack accuracy. The bitter taste of many such medicaments is also a drawback.

Solid dosage forms which are swallowed, such as tablets and capsules, provide accurate dosage and avoid taste problems; but since they have to disintegrate in the gastrointestinal tract and the medicament has then to dissolve before it can be absorbed, absorption tends to be slower than from a suspension, and may be less than complete. Also, some patients have difficulty swallowing tablets and capsules, and there is a practical limit to the size, and therefore the dose, that can be swallowed.

Single dose powders for reconstitution in sachet form, and dispersible tablets, offer the advantages of suspensions without the problems of instability, measurement inaccuracy, difficulty in swallowing, or size limitation. However, residues from the dispersed formulation may be another reason for incomplete doses being swallowed. This is a particular problem with dispersible tablets, since the component granules may disperse into particles which are too large to remain evenly suspended.

In general, chewable tablets are advantageous in that they combine the accuracy of dosage associated with tablets, with the optimum bioavailability of suspensions. They may also accommodate larger doses than swallow tablets or capsules. Their acceptability is, however, reduced for bitter tasting medicaments, such as antibiotics, especially at higher doses, for example 500 mg. and above.

The dispersion properties of dispersible tablets can be facilitated by the inclusion of an acid/base couple in which the base liberates carbon dioxide when the components of the couple are dissolved in water. Such an effervescent couple has also been included in tablets for swallowing, to aid their disintegration in the gastrointestinal tract. It is also known to provide effervescent formulations of medicaments in water-soluble form so as to provide clear solutions of the antibiotics.

It has now been found that the inclusion of an effervescent couple in chewable tablets of bitter-tasting medicaments has surprising advantages with respect to palatability, in addition to assisting the break-up of the tablets in the mouth when chewed or sucked. Such 'fizzy chewable' tablets are thus well-accepted by patients, especially small children, who would otherwise find the medicine difficult to take and who might therefore refuse treatment. This contribution to improved patient compliance is also important with other classes of patients, for example the elderly, and those with mental illness.

Accordingly in one aspect the present invention provides a chewable tablet comprising a chewable base, a medicament and an effervescent couple.

This chewable composition is especially suitable for improving the taste characteristics of a range of medicaments, particularly for improving the taste of bitter-tasting medicaments, but clearly also provides a pleasant mode of administering any medicament, particularly those with an unpleasant mouth-feel even in the absence of a bitter taste, for example antacids.

Typical bitter-tasting medicaments are β-lactam antibiotics including penicillins such as amoxycillin or ampicillin, optionally in admixture with a β-lactamase inhibitor especially when a high dose is needed. Other medicaments whose taste can be improved include antihistamine $H_2$-receptor antagonists typically anti-ulcer compounds such as cimetidine, non-steroidal anti-inflammatories such as nabumetone, and bile acid sequestrants.

The effervescent couple comprises a basic ingredient and an acidic ingredient, the basic ingredient liberating carbon dioxide when it and the acidic ingredient are contacted with saliva or added water.

The amount of the effervescent couple is selected at a level sufficient to counter the taste of the medicament without itself causing discomfort in the patients mouth. Normally the amount of effervescent couple will be less than that conventionally used in water-dispersible or solubilizable tablets.

Preferred antibiotics are amoxycillin and ampicillin, preferably amoxycillin trihydrate. A preferred β-lactamase inhibitor is clavulanic acid, preferably as potassium clavulanate. Typically, the ratio of antibiotic to inhibitor is 4:1 or 2:1 by weight, but ratios of 12:1 to 1:1 may be used. The weight of antibiotic in a unit dose may range from 125 mg to 1 g, expressed in terms of the activity of the antibiotic. The weight of antibiotic in the composition calculated as the free acid, may range from 5% to 50% based on the weight of the tablet. The weight of the β-lactamase inhibitor in the composition, calculated as the acid, may range from 0.4% to 30% based on the weight of the tablet.

Other medicaments used in the tablet of the invention will also typically comprise 5 to 50% of the tablet weight.

The effervescent couple typically comprises citric acid or sodium hydrogen citrate and sodium bicarbonate, but other physiologically acceptable acid/alkaline or alkaline earth metal carbonate mixtures may be used, for example tartaric, adipic, fumaric or malic acids, and sodium, potassium or calcium (bi)carbonates or sodium glycine carbonate.

In general it has been found that preferred taste characteristics are exhibited when the relative proportions of the components of the effervescent couple on a chemical molecular equivalent basis are in the range of 4:3 to 1:3, more preferably about 2:3, expressed as the ratio of molecular equivalent of the acidic component to the basic component. In terms of a preferred combination of citric acid and sodium bicarbonate these values represent on a weight basis, a range from 1:1 to 0.3:1, preferably 0.5:1 expressed as the ratio of acidic to basic component.

However, in some formulations, the choice of flavouring agents may result in optimisation of taste characteristics when there is an excess of acidic component, for example, on a chemical molecular equivalent basis of from about 11:3 to 4:3 expressed as the ratio of acidic to basic component. For the combination of citric acid and sodium bicarbonate this represents 5:1 to 1:1 on a weight basis.

The weight of the acidic component may be in the range 0.5% to 20%, preferably 1.5% to 5%, of the weight of the tablet.

The weight of the basic component may be in the range 0.5% to 30%, preferably 1.5% to 10%, of the weight of the tablet.

In general, taste testing shows that acceptable taste characteristics are found with the effervescent couple representing 6.25% to 30% of the final tablet weight, with a preference for 10–15% in chewable antibiotics tablets but up to 20% for some other materials, such as nabumetone.

Preferred combinations comprise citric acid (or sodium hydrogen citrate) or malic acid with sodium carbonate in a weight ratio of 0.5:1 to 1:1.

The chewable base may be any of those conventionally employed in chewable tablets, for example mannitol, sorbitol, dextrose, fructose or lactose alone or in combination. The tablets may also contain conventional lubricants such as magnesium stearate, sweetening agents such as sodium saccharin and aspartame, and flavouring and colouring agents.

In another aspect of this invention disintegrating agents are incorporated into the chewable tablet so as to give the patient the option of dispersing the tablet in a small amount of water prior to administration.

Suitable disintegrating agents are cellulose products such as microcrystalline cellulose, microfine cellulose or hydroxy propyl cellulose, and other materials such as cross-linked polyvinyl pyrrolidone (PVP) or sodium starch glycollate, used singly or in admixture. Hitherto in attempts to provide a dispersible tablet which can also be chewed containing conventional, especially cellulose-based disintegrants, the latter impart an unpleasant mouth-feel. However this is masked effectively when combined with an effervescent couple in the chewable tablets of this invention.

When using disintegrating agents to impart dispersibility to the chewable tablets, the amount of effervescent couple may be maintained at the levels indicated above relative to the weight of the final chewable, dispersible tablet. In view of the additional taste load, amounts of effervescent couple in the upper regions of the indicated ranges may be preferred.

The disintegrant is typically added at amounts of 5% to 30%, preferably from 15 to 20%, based on the final weight of the tablet.

The ingredients discussed above may be formed into tablets by conventional techniques, for example either by direct compression, or first slugging some of the ingredients, milling the slugs, blending with the remaining ingredients, and then compressing, as appropriate.

The chewable tablets are preferably packaged in sealed protective containers, such as screw cap bottles, plastic or metal tubes, aluminium foil sachets, aluminium-foil backed blister packs. It may be appropriate to incorporate a desiccant in the packaging. Alternatively, an edible desiccant may be incorporated in the composition as disclosed in EP-A-0 049 061 (Beecham).

Preferably the tablets are in unit-dose form. The amount of medicament in a unit-dose will depend on the condition to be treated and the assay of the medicament. The unit-dose will be repeated according to the usual regime for the medicament.

The invention is illustrated by the following Examples.

EXAMPLE 1

250 mg Dose Fizzy Chewable Tablet

β-Lactam Antibiotic

| Ingredients | mg/tablet | (% w/w) |
|---|---|---|
| Amoxycillin Trihydrate equivalent to Amoxycillin free acid | 250.00 | 41.667 |
| Magnesium stearate | 6.75 | 1.125 |
| Citric acid | 12.50 | 2.083 |
| Sodium bicarbonate | 25.00 | 4.167 |
| Sodium saccharin | 2.50 | 0.417 |
| Lemon dry flavour | 27.50 | 4.583 |
| Lime dry flavour | 1.38 | 0.230 |
| Sorbitol B.P. | 90.00 | 15.000 |
| Mannitol U.S.P. | q.s. to 100% | |
| | 600 mg | |

EXAMPLE 2

375 mg Dose Fizzy Chewable Tablet

β-Lactam Antibiotic+β-Lactamase Inhibitor

| Ingredient | mg/tablet | (% w/w) |
|---|---|---|
| Amoxycillin Trihydrate equivalent to Amoxycillin free acid | 250.00 | 20.833 |
| Potassium Clavulanate equivalent to clavulanic acid | 125.00 | 10.417 |
| Magnesium stearate | 12.0 | 1.000 |
| Citric acid | 17.5 | 1.458 |
| Sodium bicarbonate | 35.0 | 2.917 |
| Sodium saccharin | 5.0 | 0.417 |
| Lemon dry flavour | 50.0 | 4.167 |
| Lime dry flavour | 2.5 | 0.208 |
| Sorbitol B.P. | 180.00 | 15.000 |
| Silica gel dessicant | 80.0 | 6.667 |
| Mannitol U.S.P. | q.s to 100% | |
| | 1200 mg | |

Manufacturing Procedure for Examples 1, 2, and 3

All ingredients were reduced to the desired particle size by milling, then blended in a planetary mixer, to produce a compression mix. The compression mix was then tabletted on a rotary tabletting press, to the desired tablet weight.

EXAMPLES 3A and 3B 500 mg NSAID Fizzy Chewable Tablets

| Ingredients | A mg | B mg |
|---|---|---|
| Nabumetone | 500.00 | 500.00 |
| Sodium Bicarbonate | 50.00 | 50.00 |
| Citric Acid Anhydrous Ph. Eur. | 25.00 | 25.00 |
| Sorbitol B.P. | 180.00 | 180.00 |
| Magnesium Stearate Ph. Eur. | 13.50 | 13.50 |
| Lemon Dry Flavour | 55.00 | — |
| Peppermint Flavour | — | 12.00 |
| Vanilla Flavour | — | 12.00 |
| Saccharin Sodium B.P. | 5.00 | 5.00 |
| Mannitol USP | 1200.00 to | 1200.00 |

EXAMPLE 4

β-Lactam Antibiotic/β-Lactamase Inhibitor Fizzy Chewable Dispersible Tablet

EXAMPLE 4A

| EXCIPIENTS | Mg Per Tablet | % |
|---|---|---|
| *Amoxycillin Trihydrate (fa) | 250.0 | 20.83 |
| *Potasium Clavulanate (fa) | 62.5 | 5.21 |
| *Magnesium Stearate | 12.0 | 1.00 |
| *Citric Acid | 48.0 | 4.00 |
| *Sodium Bicarbonate | 62.4 | 5.20 |
| *Silica Gel Dessicant | 38.4 | 3.20 |
| PVP Cross-Linked Dried | 72.0 | 6.00 |
| Aspartame | 16.8 | 1.40 |
| Lemon Flavour | 28.8 | 2.40 |
| Lime Flavour | 4.8 | 0.40 |
| Mannitol | to 1200.0 | to 100.00 |

* = Slugging mixture

EXAMPLE 4B

| EXCIPIENTS | Mg Per Tablet | % |
|---|---|---|
| *Amoxicillin Trihydrate (fa) | 250.0 | 20.83 |
| *Potasium Clavulanate (fa) | 62.5 | 5.21 |
| *Magnesium Stearate | 12.0 | 1.00 |
| *Citric Acid Anhydrous | 48.0 | 4.00 |
| *Sodium Bicarbonate | 62.4 | 5.20 |
| *Silica Gel Dessicant | 38.4 | 3.20 |
| PVP Cross-Linked Dried | 72.0 | 6.00 |
| Aspartame | 16.8 | 1.40 |
| Orange Flavour | 25.0 | 2.08 |
| Pineapple Flavour | 10.0 | 0.83 |
| Mannitol | to 1200.0 | to 100.00 |

* Slugging Mixture

EXAMPLE 4C

| EXCIPIENTS | Mg Per Tablet | % |
|---|---|---|
| *Amoxycillin Trihydrate (fa) | 250.0 | 20.83 |
| *Potasium Clavulanate (fa) | 62.5 | 5.21 |
| *Magnesium Stearate | 12.0 | 1.00 |
| *Citric Acid | 48.0 | 4.00 |
| *Sodium Bicarbonate | 62.4 | 5.20 |
| *Silica Gel Dessicant | 38.4 | 3.20 |
| PVP Cross-Linked Dried | 72.0 | 6.00 |
| Microcrystalline cellulose | 150.0 | 12.50 |
| Aspartame | 16.8 | 1.40 |
| Lemon Flavour | 28.8 | 2.40 |
| Lime Flavour | 4.8 | 0.40 |
| Mannitol | to 1200.00 | to 100.00 |

* = Slugging mixture

EXAMPLE 4D

| EXCIPIENTS | Mg Per Tablet | % |
|---|---|---|
| *Amoxycillin Trihydrate (fa) | 250.0 | 20.83 |
| *Potasium Clavulanate (fa) | 62.5 | 5.21 |
| *Magnesium Stearate | 12.0 | 1.00 |
| *Citric Acid Anhydrous | 48.0 | 4.00 |

-continued

| EXCIPIENTS | Mg Per Tablet | % |
|---|---|---|
| *Sodium Bicarbonate | 62.4 | 5.20 |
| *Silica Gel Dessicant | 38.4 | 3.20 |
| PVP Cross-Linked Dried | 72.0 | 6.00 |
| Microcrystalline cellulose | 150.0 | 12.50 |
| Aspartame | 16.8 | 1.40 |
| Orange Flavour | 25.0 | 2.08 |
| Pineapple Flavour | 10.0 | 0.83 |
| Mannitol | to 1200.0 | to 100.00 |

* Slugging Mixture

Manufacturing Procedure for Examples 4A/B/C/D

The materials marked * were slugged on a tabletting machine. The 'slugs' thus obtained were broken down by milling and then blended with the remaining ingredients to produce a compression mix. This mix was tabletted on a rotary tabletting machine to the desired tablet weight.

We claim:

1. A tablet comprising a chewable base, nabumetone and an effervescent component comprised of an acid component and an alkaline component, wherein the nabumetone comprises at least 50% by weight of said tablet.

2. A chewable tablet comprising a chewable base, wherein said chewable base contains at least one member selected from the group consisting of mannitol, sorbitol, dextrose, fructose, and lactose, nabumetone, in an amount of at least 50% by weight, and an effervescent couple in which said effervescent couple comprises an acidic component comprising 0.5% to 20% by weight of said tablet wherein said acidic component is selected from the group consisting of citric acid tartaric acid, adipic acid, fumaric acid and malic acid, and acid salts thereof, and a base component comprising 0.5% to 30% by weight of said tablet, wherein said basic component is selected from the group consisting of sodium, potassium and calcium (bi) carbonates and sodium glycine carbonate, the effervescent couple comprising 1.0 to 30% of the weight of said tablet.

3. A tablet comprising a chewable base, nabumetone and an effervescent component comprised of an acid component and an alkaline component, wherein the nabumetone comprises at least 50% by weight of said tablet, and wherein the tablet further comprises as a disintegrating agent a member selected from the group consisting of sodium starch glycolate, microcrystalline cellulose, and PVP, or mixtures thereof.

4. The chewable tablet according to claim 1 wherein the chewable base contains at least one member selected from the group consisting of mannitol, sorbitol, dextrose, fructose, and lactose.

5. The chewable tablet according to claim 1 wherein the acid component of the effervescent couple comprises 0.5% to 20% by weight of said tablet.

6. The chewable tablet according to claim 5 wherein the acid component is selected from the group consisting of citric acid, tartaric acid, adipic acid, fumaric acid and malic acid, and acid salts thereof.

7. The chewable tablet according to claim 1 wherein the alkaline component of the effervescent couple comprises 0.5% to 30% by weight of said tablet.

8. The chewable tablet according to claim 7 wherein the alkaline component is selected from the group consisting of sodium, potassium and calcium (bi) carbonates and sodium glycine carbonate.

9. The chewable tablet according to claim 1 wherein the effervescent component comprises 1.0 to 30% of the weight of said tablet.

10. The chewable tablet according to claim 1 wherein the acidic component of the effervescent couple to the alkaline component of the effervescent couple is from about 4:3 to about 1:3, on a molecular equivalent basis.

11. The chewable tablet according to claim 1 wherein the effervescent couple comprises citric acid, sodium hydrogen ciytrate or malic acid with sodium bicarbonate in a weight ratio (acid:base) of 0.5:1 to 1:1.

12. The chewable tablet according to claim 1 which further comprises a disintegrating agent selected from the group consisting of sodium starch glycolate, microcrystalline cellulose, and PVP, or mixtures thereof.

* * * * *